United States Patent [19]

Nordquest

[11] Patent Number: 4,743,230
[45] Date of Patent: May 10, 1988

[54] INFLATING AND DEFLATING DEVICE FOR BALLOON DILATATION CATHETERS

[75] Inventor: Richard A. Nordquest, Del Mar, Calif.

[73] Assignee: Advanced Cardiovascular Systems, Inc., Mountain View, Calif.

[21] Appl. No.: 772,715

[22] Filed: Sep. 5, 1985

[51] Int. Cl.[4] .............................................. A61M 5/00
[52] U.S. Cl. ...................................... 604/97; 604/224
[58] Field of Search ..................... 604/97, 98, 99, 224, 604/227; 92/33

[56] References Cited

U.S. PATENT DOCUMENTS

| | | | |
|---|---|---|---|
| 938,544 | 11/1909 | Ball | 604/224 |
| 2,585,815 | 2/1952 | McLintock | 604/224 |
| 2,874,877 | 2/1959 | Spencer | 222/390 X |
| 4,370,982 | 2/1983 | Reilly | 604/98 |
| 4,439,185 | 3/1984 | Lundquist | 604/97 |

*Primary Examiner*—Stephen C. Pellegrino
*Attorney, Agent, or Firm*—Fulwider, Patton, Rieber, Lee & Utecht

[57] ABSTRACT

Inflating and deflating device for a balloon dilatation catheter comprising a housing and a syringe carried by the housing. The syringe has an outlet adapted to be connected to the catheter. The syringe includes a container and a piston which is slidably mounted in the container. The syringe also includes a rigid plunger connected to the piston and extends out of the housing. The plunger has helical threads formed thereon to provide an elongate ratchet. A pawl is movable between ratchet-engaging and ratchet-disengaging positions. A spring is carried by the housing and engages the pawl and yieldably urges the pawl into its ratchet-engaging position. A tab is carried by the housing and engages the pawl and is used for moving the pawl out of engagement with the ratchet to release the ratchet. The pawl and the ratchet are formed so that when the syringe contains a liquid, the plunger can be pushed inwardly by hand to provide a desired pressure on the liquid in the container and the plunger can be rotated to gradually increase or decrease the pressure on the liquid in the container.

5 Claims, 1 Drawing Sheet

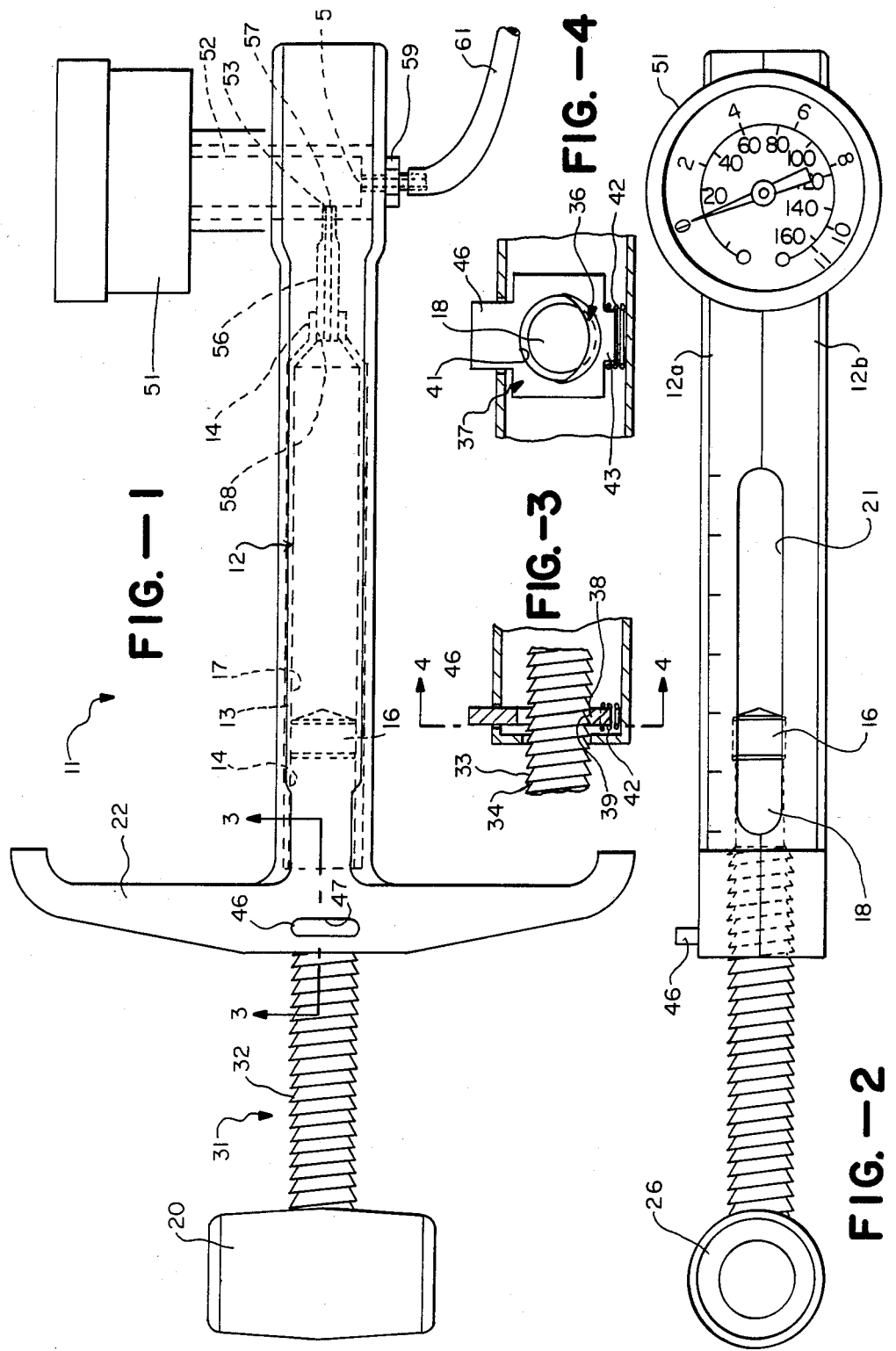

1

INFLATING AND DEFLATING DEVICE FOR BALLOON DILATATION CATHETERS

This invention relates to an inflating and deflating device and, more particularly, to an inflating and deflating device for balloon dilatation catheters.

Inflating and deflating devices for balloon dilatation catheters have heretofore been provided. For example, there is disclosed in U. S. Pat. No. 4,439,185 an inflating and deflating device for balloon dilatation catheters which has met with great success. There still, however, is a need to simplify such devices and also to provide a greater range of adjustments for increasing the pressures which can be provided by the device. There is therefore a need for a new and improved inflating and deflating device for balloon dilatation catheters.

In general, it is an object of the present invention to provide an inflating and deflating device for balloon dilatation catheters which facilitates obtaining desired pressures.

Another object of the invention is to provide a device of the above character which makes it possible to provide fine adjustment of the pressure.

Another object of the invention is to provide a device of the above character in which a ratchet and pawl mechanism is utilized for making adjustments to the pressure in such a manner as to minimize the hand-held motions necessary in making such pressure adjustments.

Additional objects and features of the invention will appear from the following description in which the preferred embodiment is set forth in detail in conjunction with the accompanying drawing.

FIG. 1 is a side elevational view of an inflating and deflating device incorporating the present invention.

FIG. 2 is a top plan view of the inflating and deflating device shown in FIG. 1.

FIG. 3 is a cross sectional view taken along the line 3—3 of FIG. 1.

FIG. 4 is a cross sectional view taken along the line 4—4 of FIG. 3.

In general, the inflating and deflating device incorporating the present invention is for use with a balloon dilatation catheter. It is comprised of a housing and a syringe carried by the housing. The syringe consists of a liquid container which is adapted to be connected to the catheter. The syringe also consists of a piston which is disposed in the container and is movable longitudinally of the container. A rigid plunger is connected to the piston for operating the piston and extends out of the housing. The plunger is provided with helical threads formed externally on the same to provide an elongate ratchet. A pawl movable between the rachet-engaging and ratchet-disengaging positions is provided. Spring means is carried by the housing and engages the pawl for yielding urging the pawl into the ratchet engaging position. A handle is carried by the housing and a button is carried by the plunger. The plunger is adapted to be engaged by the palm of the hand while the fingers of the hand engage the handle. Compression of the palm and fingers forces the plunger/piston into the cylinder while the pawl engages the threads of the plunger under the yieldable force of the spring means. The pawl and the ratchet are formed so that when the cylinder contains a liquid the plunger can be pushed inwardly by hand to provide a desired pressure on the liquid. The desired pressure on the liquid is maintained because the pawl engages the helical threads of the plunger. The plunger can be rotated to gradually increase or decrease the pressure on the liquid in the container.

More, in particular, the inflating and deflating device 10 consists of a housing 11 formed of a suitable material such as plastic and a syringe 12 which is carried by the housing 11. The syringe 12 consists of a container 13 in the form of a cylinder which is disposed within the housing. The container 13 is provided with an internally threaded outlet 14 which is adapted to be connected to subsequent in-line parts as hereinafter described. A piston 16 is mounted on the plunger and is slidable longitudinally of the interior volume 17 of the container. The interior volume 17 can be of a suitable size, as for example 10 cc. A plunger 18 carries the piston 16 and extends out one end of the housing 11.

The housing 11 is formed in two parts 11a and 11b to facilitate assembly of the device. The housing 11 is provided with two elongate openings 21 which extend longitudinally of the housing. The housing 11 is provided with a tee-shaped handle 22 which has two portions 22a and 22b extending outwardly in opposite directions. The handle 22 is formed so that the fingers of the human hand are adapted to grasp the handle. A cylinder-like button 26 is mounted on the end of the plunger 18. The button 26 is adapted to be engaged on the palm of the hand while the fingers of the same hand engage the handle 22.

A ratchet 31 is formed on the plunger 18 by providing helical tapered threads 32 extending longitudinally on the plunger 18. The threads 32 are of a modified buttress type and are formed with surfaces 33 and 34 with the surfaces 33 extending at an angle of approximately 35° from the horizontal and the surfaces 34 extending at an angle of approximately 90° from the horizontal.

A pawl 36 is provided which is movable between ratchet engaging and ratchet disengaging positions. The pawl 36 is formed as a part of the cross-shaped member 37 (see FIG. 4) which is provided with a vertical surface 38 that is adapted to come into engagement with the vertical surfaces 34 of the ratchet 31. It is also provided with an inclined surface 39 which is adapted to engage the inclined surfaces 33 of the ratchet 31. The vertical surface 38 is substantially vertical whereas the inclined surface 39 extends at an angle of approximately 35° from the horizontal. The pawl 36 is arcuate shaped and forms a part of a circular opening 41 provided in the member 37. Yieldable means in the form of two springs 42 is provided for yieldably urging the pawl 36 into the ratchet engaging position. Each of the springs 42 has one end of the same engaging the housing 11 and has the other end fitted over a rectangular protrusion formed as a part of the member 37.

Means is provided for urging the pawl 36 out of the rachet-engaging position to a ratchet disengaging position against the force of the yieldable means provided by springs 42 and consists of a tab 46 which is generally rectangular in shape and which is provided as a portion of the member 37. The tab 46 extends through a slot 47 provided in the housing 11 in the vicinity of the handle 22.

A pressure gauge 51 is mounted on the distal extremity of the housing 11. The pressure gauge 51 is of a conventional type and can measure pressures ranging from less than zero to approximately 200 psi and, if desired, the pressure range can be increased to 250 psi. The pressure gauge 51 is provided with a gauge body 52 which extends into the distal extremity of the housing 11. The gauge body 52 is provided with threaded bores 53 and 54. A transition tube 56 is provided with an exteriorly threaded portion 57 which is threaded into the threaded bore 53 in the gauge body 52. Similarly, it is provided with a externally threaded portion 58 which is threaded into the internally threaded outlet 14 of the syringe 12. A fitting 59 is threaded into the internally threaded bore 54 of the gauge body 52. A flexible tube 61 is connected to the fitting 59 and is adapted to be connected to a conventional balloon dilatation catheter 10 (not shown).

Operation and use of the inflating and deflating device 10 may now be briefly described as follows. Let it be assumed that the interior volume 17 of the container 13 has been filled with a radiopaque contrast liquid of a conventional type by connecting the tube 61 to a source of such liquid. The handle 22 can be held in one hand and the button 26 grasped by the other hand and the piston 16 retracted to create a vacuum condition and to bring the radiopaque contrast liquid into the container to fill the same. This can be readily accomplished by depressing the tab 46 to cause the pawl 36 to be moved out of the way of the threads 32. As soon as a sufficient quantity of radiopaque contrast liquid has been drawn into the container 13, the tube 61 can be connected to a conventional balloon dilatation catheter.

Pressure can then be applied to the plunger 18 to cause it to be moved inwardly. As the plunger is moved inwardly, the pawl 36 of the ratchet 31 will be cammed out of the way successively by the inclined surfaces 33 against the force of the springs 42 and will engage each of the generally vertical surfaces 34 of the threads 32 under the force of the springs 42. The ratchet 31 thus serves to hold the plunger in position as it is advanced. The inflation pressure created within the liquid container 13 therefore will be maintained. Typically, the plunger is pressed inwardly until approximately the desired pressure for inflating the balloon as, for example, 100 to 150 psi has been reached. Thereafter, a fine adjustment of the pressure can be obtained by rotating the button 26 and the plunger 18 to further progressively advance or retract the plunger by the engagement of the pawl with the threads 32. Rotation of the button 21 is continued until the desired pressure is reached. Thus it can be seen that a rough adjustment of the pressure can be readily obtained by pressing the plunger 18 inwardly by the hand engaging the handle 22 and the button 26 and thereafter a fine adjustment can be obtained by rotation of the button 26 and the plunger 18.

When it is desired to release the pressure on the balloon, the tab 46 can be depressed to urge the pawl 36 out of engagement with the ratchet 31 permitting the plunger 18 to be retracted and to deflate the balloon by withdrawing liquid from the balloon. As explained previously, this retraction can be readily accomplished because when the pawl 36 is held in a depressed position by the hand engaging and depressing the tab 46 against the force of the springs 42.

It is apparent that the inflating and deflating device can be utilized for inflating the balloons of dilatation catheters inside and outside of the human body. It is particularly advantageous for inflating the balloons within a stenosis in the human body because of the precise adjustment of pressure which can be obtained.

The device is constructed in such a manner so that it is relatively compact. It can be formed of relatively inexpensive materials so that it can be discarded if necessary after it has been utilized in connection with a angioplasty procedure.

It should be appreciated that if desired, the transition tube 56 can be eliminated and the syringe 12 fabricated in such a manner so that it can be threaded directly into the gauge body 52 of the gauge 51 thereby eliminating the necessity for the transition tube.

It is apparent from the foregoing that there has been provided an inflating and deflating device for the inflation of balloon dilatation catheters which has a number of desirable features. As explained above, it is possible to achieve and maintain a desired pressure with relative ease.

What is claimed is:

1. In an inflating and deflating device for a balloon dilatation catheter, a housing, a syringe carried by the housing, the syringe having an outlet adapted to be connected to the catheter, the syringe comprising a container and a piston slidably mounted in the container, the syringe also including a rigid plunger connected to the piston and extending out of the housing, said plunger having tapered helical threads formed thereon to provide an elongate ratchet, a pawl movable between rachet-engaging and rachet-disengaging positions, yieldable means carried by the housing and engaging the pawl and yieldably urging the pawl into its rachet-engaging position, and means carried by the housing and engaging the pawl for moving the pawl out of engagement with the ratchet to release the ratchet, the pawl and the ratchet being formed so that when the syringe contains a liquid, the plunger can be pushed inwardly by hand so that the tapered threads cause the pawl to be cammed outwardly against the force of the yieldable means to cause the piston to provide a desired pressure on the liquid in the container or alternatively the plunger can be rotated with the pawl in engagement with the threads to cause gradual movement of the piston to gradually increase or decrease the pressure on the liquid in the container.

2. A device as in claim 1 together with a handle carried by the housing and a button adapted carried by the plunger, the button being adapted to be engaged by the palm of the hand while the fingers of the hand are adapted to engage the handle and another finger of the hand is capable of engaging the means for moving the pawl out of engagement with the ratchet.

3. A device as in claim 1 wherein said pawl is formed as a part of a rectangular member disposed in the housing, the rectangular member having a hole therein, the pawl being arcuate in shape and forming a portion of a circular opening extending through the member, the plunger being disposed within said hole.

4. A device as in claim 3 wherein said yieldable means is in the form of a spring having one end engaging the housing and having the other end engaging said member.

5. In an inflating and deflating device for a balloon dilatation catheter, a housing, a syringe carried by the housing, the syringe having an outlet adapted to be connected to the catheter, the syringe being a container and a piston slidably mounted in the container, the syringe also including a rigid plunger connected to the piston and extends out of the housing, said plunger having tapered helical threads formed thereon to provide an elongate ratchet, a pawl movable between ratchet-engaging and rachet-disengaging positions, yieldable means carried by the housing and engaging the pawl and yieldably urging the pawl into its rachet-engaging position, and means carried by the housing and engaging the pawl for moving the pawl out of engagement with the ratchet to release the ratchet, the pawl and the ratchet being formed so that when the syringe contains a liquid, the plunger can be pushed inwardly by hand so that the tapered helical threads cause the pawl to be cammed outwardly against the force of the yieldable means to provide a desired pressure on the liquid in the container or the plunger can be rotated to gradually increase or decrease the pressure on the liquid in the container, the threads forming said ratchet having generally vertical surfaces extending approximately perpendicular to the longitudinal axis of the plunger and having other surfaces extending at an angle of approximately 35° with respect to the longitudinal axis of the plunger, said pawl being provided with a substantially vertical surface adapted to engage the generally vertical surfaces of the threads of the ratchet to lock the ratchet in a predetermined position.

* * * * *